(12) United States Patent
Dunkley et al.

(10) Patent No.: US 9,498,525 B2
(45) Date of Patent: Nov. 22, 2016

(54) TREATMENT OR PROPHYLAXIS OF ASTHMA

(75) Inventors: Margaret Dunkley, Elermore Vale (AU); Robert Clancy, North Sydney (AU); Allan William Cripps, Robina (AU); Diana Christine Otczyk, Robina (AU)

(73) Assignee: HUNTER IMMUNOLOGY LIMITED, Sydney, New South Wales (AU)

( * ) Notice: Subject to any disclaimer, the term of this patent is extended or adjusted under 35 U.S.C. 154(b) by 640 days.

(21) Appl. No.: 12/531,402

(22) PCT Filed: Mar. 14, 2008

(86) PCT No.: PCT/AU2008/000358
§ 371 (c)(1),
(2), (4) Date: Jan. 15, 2010

(87) PCT Pub. No.: WO2008/109956
PCT Pub. Date: Sep. 18, 2008

(65) Prior Publication Data
US 2010/0150967 A1    Jun. 17, 2010

(30) Foreign Application Priority Data
Mar. 15, 2007  (AU) .............................. 2007901326

(51) Int. Cl.
*A61K 39/02* (2006.01)
*A01N 63/00* (2006.01)
*C12N 1/00* (2006.01)
*A61K 39/102* (2006.01)

(52) U.S. Cl.
CPC .................... *A61K 39/102* (2013.01)

(58) Field of Classification Search
USPC ...................... 424/256.1, 93.1, 93.4; 435/243
See application file for complete search history.

(56) References Cited

U.S. PATENT DOCUMENTS 4,873,090 A    10/1989 Clancy
7,776,850 B2   8/2010 Borody

OTHER PUBLICATIONS

Clancy et al (Lancet 1985. 2:8469-70).*
Arandjus et al (Resp. Medicine. 2006, 100: 1671-81).*
Schreurs et al (Euro. J. Pharmacology. 1982. 77(2-3): 95-102).*
Schreurs et al (Naunyn-Schmiedeberg's Archives of Pharmacology. 1982. 320(3): 235-9).*
Toews, G.B. et al (Eur. Respir. Rev. 2005. 14(95): 62-28).*
Kramarz et al (J.Pediatrics. 138(3): 306-310).*
Abe Y, Murphy TF, Sethi S, Faden HS, Dmochowski J, Harauchi Y, Thanavala YM. Lymphocyte proliferative response to P6 of Haemophilus influenzae is associated with relative protection from exacerbations of chronic obstructive pulmonary disease. Am J Respir Crit Care Med 2002; 165: 967-71.
Clementsen P, Milman N, Kilian M. et al. Endotoxin from Haemophilus influenzae enhances IgE-mediated and non-immunological histamine release. Allergy 1990; 45: 10-17.
Courcol RJ, Damien JM, Ramon P, C Voisin C, Martin GR. Presence of alveolar macrophages as a criterion for determining the suitability of sputum specimens for bacterial culture. Eur J Clin Microbiol 1985; 3: 122-25.
Kjaergard LL, Larsen FO, Norn S, Clementsen P, Stahl Skov P, Permin H. Basophil-bound IgE and serum IgE directed against Haemophilus influenzae and *Streptococcus pneumoniae* in patients with chronic bronchitis during acute exacerbations. APMIS 1996; 104: 61-67.
Kyd JM, Taylor D, Cripps AW. Conservation of immune responses to proteins isolated by preparative polyacrylamide gel electrophoresis from the outer membrane of nontypable Haemophilus influenzae. Infect Immun 1994; 62: 5652-58.
Moller LVM, Timens W, van der Bij W et al. Haemophilus influenzae in lung explants of patients with end-stage pulmonary disease. Am J Respir Crit Care Med 1998; 157: 950-56.
Murphy TF, Bartos LC. Purification and analysis with monoclonal antibodies of P2, the major outer membrane protein of nontypable Haemophilus influenzae. Infect Immun 1988; 56:1084-89.
Murphy TF, Brauer AL, Schiffmacher AT, Sethi S. Persistent colonization by Haemophilus influenzae in chronic obstructive pulmonary disease. Am J Respir Crit Care Med 2004; 170: 266-72.
Nelson, M.B., M.A. Apicelli., Murphy, T.F., Vankeulen, H., Spotila, L.D., Rekosh, D. Cloning and sequencing of Haemophilus influenza outer membrane protein P6. Infect. Immun. 1988; 56: 128-134.
Norn S, Jensen L, Kjaergard LL, Permin H, Stahl Skov P, Espersen F. Bacteria-induced IgE-mediated histamine release: Examination of patients with chronic bronchitis (CB) during acute exacerbations. Agents Actions 41, Special Conference Issue 1994: C22-C23.
Pauwels R, Verschraegen G, Van Der Straiten M. IgE antibodies to bacteria with bronchial asthma. Allergy 1980; 157: 665-9.
Rhode G, Gevaert P, Holtappels G et al. Increased IgE-antibodies to *Staphylococcus aureus* enterotoxins in patients with COPD. Respir Med 2004; 98: 858-64.
Seggev JS, Sedmak GV, Kurup VP. Isotype-specific antibody responses to acute Mycoplasma pneumoniae infection. Ann Allergy Asthma Immunol 1996; 77: 67-73.
Sethi S, Murphy TF. Bacterial infection in chronic obstructive pulmonary disease in 2000: a state-of-the-art review. Clin Microbiol Rev 2001; 14: 336-363.
Shen J, Brackett R, Fischer T, Holder A, Kellogg F, Michael JG. Specific Pseudomonas immunoglobulin E antibodies in sera of patients with cystic fibrosis. Infect Immun 1981; 32: 967-68.

(Continued)

Primary Examiner — Jennifer Graser
(74) Attorney, Agent, or Firm — Pergament & Cepeda LLP; Milagros A. Cepeda; Edward D. Pergament

(57) ABSTRACT

There is provided a method for prophylaxis or treatment of asthma in an individual. The method comprises administering to the individual an effective amount of a Non-typable *Haemophilus influenzae* (NTHi) vaccine. The vaccine is typically an oral whole killed NTHi vaccine.

7 Claims, 2 Drawing Sheets

(56) References Cited

OTHER PUBLICATIONS

Simpson, J.L., Scott, R., Boyle, M.J., Gibson, P.G. Inflammatory subtypes in asthma: Assessment and identification using induced sputum. Respirology 2006; 11, 54-61.
Tee RD, Pepys J. Specific IgE serum antibodies to bacterial antigens in allergic lung disease. Clin Allergy 1982; 12: 439-50.
Welliver RC, Wong DT, Middleton E Jr, Sun M, McCarthy N, Ogra PL. Role of parainfluenza virus-specific IgE in pathogenesis of croup and wheezing subsequent to infection. J Pediatrics 1982; 101: 889-96.
International Search Report and Written Opinion of International Application No. PCT/AU08/000358,filed Mar. 14, 2008, mailed on May 20, 2008.
Ahren et al., "Non-typeable Haemophilus influenzae activates Human Eosinophils through β-glucan receptors", American Journal of Respiratory Cell and Molecular Biology, 2003, pp. 598 to 605, vol. 29-issue No. 5, American Thoracic Society.
Beisswenger et al., "Allergic Airway Inflammation Inhibits Pulmonary Antibacterial Host Defense", The Journal of Immunology, 2006, pp. 1833 to 1837, vol. 177, The American Association of Immunologists, Inc.
Bisgaard et al., "Childhood Asthma after Bacterial Colonization of the Airway in Neonates", Original Article, The New England Journal of Medicine, Oct. 11, 2007, pp. 1487 to 1495, vol. 357-issue No. 15, Massachusetts Medical Society.
Epton et al., "T cell cytokine responses to outer membrane protein antigens of Haemophilus Influenzae and the house dust mite allergens Der p 1 in allergic and non-allergic subjects", Clin Exp Allergy, 2002, pp. 1589 to 1595, vol. 32, Blackwell Science Ltd.
Global Initiative for Asthma, Global Strategy for Asthma Management and Prevention, Revised 2006, pp. 1 to 96, available at www.ginasthma.org.
Harju et al., "Pathogenic bacteria and viruses in induced sputum or pharyngeal secretions of adults with stable asthma", Asthma, Thorax, 2006, pp. 579 to 584, vol. 61.
Hofer et al., "Staphylococcal Toxins Augment Specific IgE Responses by Atopic Patients Exposed to Allergen", The Journal of Investigative Dermatology, Feb. 1999, pp. 171 to 176, vol. 112-issue No. 2, The Society of Investigative Dermatology, Inc.
Kozyrsky J et al., "Increased Risk of Childhood Asthma From Antibiotic Use in Early Life", Asthma, Original Research, Chest, Jun. 2007, pp. 1753 to 1759, vol. 131-issue No. 6.
Kumar et al., "A recombinant BCG vaccine generates a Th1-like response and inhibits IgE synthesis in BALB/c mice", Immunology, 1999, pp. 515 to 521, vol. 97, Blackwell Science Ltd.
Lambert and Stern, "Infective Factors in Exacerbations of Bronchitis and Asthma", British Medical Journal, Aug. 5, 1972, pp. 323 to 327, vol. 3.
Marinaro et al., "Mucosal Adjuvant Effect of Cholera Toxin in Mice Results from Induction of T Helper 2 (Th2) Cells and IL-4", The Journal of Immunology, 1995, pp. 4621 to 4629, vol. 155, The American Association of immunologists.
Masuda et al., "Th2 Cytokine Production from Mast Cells Is Directly Induced by Lipopolysaccharide and Distinctly Regulated by c-Jun N-Terminal Kinase and p38 Pathways", The Journal of Immunology, 2002, pp. 3801 to 3810, vol. 169, The American Association of Immunologists, Inc.
Juha Pekkanen, "Commentary: Use of antibiotics and risk of asthma", International Journal of Epidemiology, 2004, pp. 564 to 565, vol. 33-issue No. 3, International Epidemiological Association.
Qadri et al., "Enterotoxin-Specific Immunoglobulin E Responses in Humans after Infection or Vaccination with Diarrhea-Causing Enteropathogens", Infection and Immunity, Oct. 2000, pp. 6077 to 6081, vol. 68-issue No. 10, American Society for Microbiology.
K Radon, The Two Sides of the "Edotoxin Coin", Occup Environ Med, 2006, pp. 73 to 78, vol. 63.
Ricci et al., "Frequency and Clinical Role of *Staphylococcus aureus* Overinfection in Atopic Dermatitis in Children", Pediatric Dermatology, Sep. 5/Oct. 2003, pp. 389 to 392, vol. 20-issue No. 5.
Sack et al., "Validation of a Volunteer Model of Cholera with Frozen Bacteria as the Challenge", Infection and Immunity, May 1998, pp. 1968 to 1972, vol. 66-issue No. 5, American Society for Microbiology.
Sergejeva et al., "Interleukin-17 as a Recruitment and Survival Factor for Airway Macrophages in Allergic Airway Inflammation", Am J Respir Cell Mol Biol, 2005, pp. 248 to 253, vol. 33.
Simpson et al., "Innate immune activation in neutrophilic asthma and bronchiectasis", Asthma, Thorax, 2007, pp. 211 to 218, vol. 62.
Solopov, "Asthma and Allergy Veritable Cause", Alternative Use to Asthma Treatment, Translated from the "Medical Newspaper" (Moscow) N 54 dated Jul. 21, 2006, Posted May 28, 2009.
Acharya et al., "Study of Isolation of Mycoplasma Pneumoniae in Asthmatics by Sputum Culture", Lung India, 2005, pp. 50 to 53, vol. 22.
Erika Von Mutius, "Of Attraction and Rejection—Asthma and the Microbial World", The New England Journal of Medicine, Oct. 11, 2007, pp. 1545 to 1547, vol. 347-issue No. 15, Massachusetts Medical Society.
Innes Asher et al., "World Allergy Organization Guidelines for Prevention of Allergy and Allergic Asthma", Condensed Version, Int Arch Allergy Immunol, Aug. 31, 2004, pp. 83 to 92, vol. 135.
Clancy et al., "Protection against recurrent acute bronchitis after oral immunization with killed Haemophilus influenzae", The Medical Journal of Australia, Apr. 16, 1990, pp. 413-416, vol. 152.
Foxwell et al., "Haemophilus influenzae oral whole cell vaccination for preventing acute exacerbations of chronic bronchitis (Review)", The Cochrane Collaboration, Reprinted 2006 (first publication 2003 by Cochrane Database of Systematic Reviews), pp. 1 to 11, Issue No. 3, John Wiley & Sons, Ltd.
Stefano Guerra, "Asthma and Chronic Obstructive Pulmonary Disease: Natural history, Phenotypes, and Biomarkers.", Curr Opin Allergy Clin Immunol., Oct. 2009, pp. 409 to 416, vol. 9-issue No. 5.
Ichinose et al., "Increase in Reactive Nitrogen Species Production in Chronic Obstructive Pulmonary Disease Airways", American Journal of Respiratory and Critical Care Medicine, 2000, pp. 701 to 706, vol. 162.
Simpson et al., "Inflammatory subtypes in asthma: Assessment and identification using induced sputum", Original Article, Respirology, 2006, pp. 54 to 61, vol. 11.
Supplementary European Search Report dated Apr. 29, 2011 for corresponding European Patent Application No. EP 08714405.
Arandjus et al., "Oral bacterial vaccines for the prevention of acute exacerbations in chronic obstructive pulmonary disease and chronic bronchitis", Evidence-Based Review, Respiratory Medicine, 2006, pp. 1671 to 1681, vol. 100, Elsevier Ltd.
Esmaily et al., "Efficacy of Immunization with Outer Membrane Proteins for Induction of Pulmonary Clearance of Nontypeable Haemophilus influenzae in a Rat Respiratory Model", Original Aricle, Iran J Allergy Asthma Immunol, Jun. 2006, pp. 57 to 61, vol. 5-issue No. 2.
Koyama et al., "Strain-Specific Pulmonary Defense Achieved after Repeated Airway Immunizations with Non-Typeable Haemophilus influenzae in a Mouse Model", Tohoku J. Exp. Med., 2007, pp. 63 to 74, vol. 211, Tohoku University Medical Press.
Notification of Decision of Rejection mailed Jun. 27, 2014, for corresponding Japanese Patent Application No. JP 2009-552975. (English Translation).
Pharma Medica, Presented by Medical Online, 2005, pp. 91 to 93, vol. 23-issue No. 11 [Reference C of the Notice of Rejection].
Haemophilus Influenzae type b, The Australian Immunization Handbook, 10th Edition, 2013.
Clancy et al., "Oral Immunization with killed Haemophilus influenzae for protection against Acute Bronchitis in chronic obstructive lung disease", Preliminary Communication, The Lancet, Dec. 21/28, 1985, pp. 1395 to 1397.
Tee and Pepys, "Specific serum IgE antibodies to bacterial antigens in allergic lung disease", Clinical Allergy, 1982, pp. 439 to 450, vol. 12, Blackwell Scientific Publications.
Zimmerman and Burns, "Childhood Immunization Guidelines: Current and Future", Well Child-Care: Issues in Prevention, Primary Care, Dec. 1994, pp. 693 to 715, vol. 21-issue No. 4.
Notification of Reasons for Rejection mailed Sep. 30, 2015, for corresponding Japanese Patent Application No. 2014-218268.

\* cited by examiner

TREATMENT OR PROPHYLAXIS OF ASTHMA

TECHNICAL FIELD

The present application relates to the administration of a bacterial vaccine for the prophylaxis or treatment of asthma.

BACKGROUND

Asthma is a chronic inflammatory condition of the airways characterised by reversible airway obstruction, and has traditionally been classified as extrinsic (due to allergic reaction to inhaled allergens such as pollens and house dust mite) or intrinsic (not due to classical allergy), the mechanism for which is unknown. This latter form of asthma has been called "idiopathic" asthma In a recently reported study based on diagnosed asthma subjects, asthma was classified based on differences in eosinophil and neutrophil counts in sputum (Simpson et al., Inflammatory subtypes in asthma: Assessment and identification using induced sputum, *Respirology* 2006; 11, 54-61). The subjects in the study were divided into different asthma subtypes based on the presence of these cell types compared to healthy control subjects. Several asthma sub-types were identified including neutrophilic asthma (>61% neutrophils) and eosinophilic asthma (>1.01% eosinophils). The neutrophilic asthma group comprised approximately 20% of the overall number of asthmatics. The study further reported persistent neutrophilia in the majority of these subjects over both short term (4 week) and long term (mean 5.3 years) intervals between sampling despite no subject reporting respiratory tract infection during the month prior to assessment. While subjects with asthma were found to have higher levels of intracellular bacteria and macrophages than healthy controls, no significant differences were found between neutrophilic asthmatics and the other asthma groups. Indeed, the levels of bacteria found were stated to be less than that consistent with acute bacterial infections, and the report concluded there was no evidence of bacterial infection to explain the inflammatory process of neutrophilic asthma.

Non-typable *Haemophilus influenzae* (NTHi) is the most common pathogenic bacteria associated with chronic bronchitis (CB) (Sethi S, Murphy T F, Bacterial infection in chronic obstructive pulmonary disease in 2000: a state-of-the-art review, *Clin Microbiol Rev* 2001; 14: 336-363). NTHi can be found in the upper airways (eg., nose, middle ear, throat and sinuses) of healthy individuals and patients with CB (Sethi, 2001) as well as several locations of the respiratory tract, including the lumen, adhering to mucosal epithelial cells in the interstitium of the submucosa (Moller et al., *Haemophilus influenzae* in lung explants of patients with end-stage pulmonary disease, *Am J Respir Crit Care Med* 1998; 157: 950-56). Studies of non-obstructive and obstructive CB have observed that a large proportion of patients have persistent infection with NTHi (Murphy T F, Bartos L C, Purification and analysis with monoclonal antibodies of P2, the major outer membrane protein of nontypable *Haemophilus* influenza, *Infect Immun* 1988; 56:1084-89).

Both NTHi and *Staphylococcus aureus* have previously been shown to induce non-IgE-mediated and enhanced IgE-mediated histamine release from mast cells obtained by broncheoalveolar lavage from the airways of patients with CB. In the case of NTHi, it has been reported that exotoxin may be responsible for the enhancement of IgE-mediated histamine release (Clementsen et al., Endotoxin from *Haemophilus influenzae* enhances IgE-mediated and non-immunological histamine release, *Allergy* 1990; 45: 10-17). Immune cells isolated from patients with CB during acute exacerbations have been shown to be both sensitized and hyperactive to the patient's own bacteria (Norn et al., Bacteria-induced IgE-mediated histamine release: Examination of patients with chronic bronchitis (CB) during acute exacerbations. *Agents Actions* 41, Special Conference Issue 1994: C22-C23). Several studies have also reported specific IgE antibodies produced in response to respiratory infection by fungi (e.g., *Aspergillus*) and viruses, (e.g., respiratory syncytial virus, parainfluenza virus), (Welliver et al., Role of parainfluenza virus-specific IgE in pathogenesis of croup and wheezing subsequent to infection. *J Pediatrics* 1982; 101: 889-96) and bacteria (e.g., S. *Pneumoniae* (Kjaergard et al., Basophil-bound IgE and serum IgE directed against *Haemophilus influenzae* and *Streptococcus pneumoniae* in patients with chronic bronchitis during acute exacerbations, *APMIS* 1996; 104: 61-67; Tee R D, Pepys J., Specific IgE serum antibodies to bacterial antigens in allergic lung disease, *Clin Allergy* 1982; 12: 439-50; Pauwels et al., IgE antibodies to bacteria with bronchial asthma, *Allergy* 1980; 157: 665-9) S. *aureus* (Rhode et al., Increased IgE-antibodies to *Staphylococcus aureus* enterotoxins in patients with COPD. *Respir Med* 2004; 98: 858-64; Tee, 1982), *Pseudomonas aeruginosa* (Shen et al., Specific *Pseudomonas* immunoglobulin E antibodies in sera of patients with cystic fibrosis. *Infect Immun* 1981; 32: 967-68), and *Mycoplasma pneumoniae* (Seggev et al., Isotype-specific antibody responses to acute *Mycoplasma pneumoniae* infection. *Ann Allergy Asthma Immunol* 1996; 77: 67-73)). IgE antibodies specific for NTHi have also been identified in the serum of patients with CB (Kjaergard, 1996; Tee 1982) and cystic fibrosis (Tee, 1982).

In a study of patients with bronchial asthma, IgE antibodies to NTHi were found in 29%. Antibodies to NTHi and/or *Streptococcus pneumoniae* were also present in 22% of patients with no other IgE mediated hypersensitivity. However, higher levels of IgE bacterial antibodies were found in patients with demonstrable IgE antibodies to various inhalant antigens (suggesting an allergic phenotype) (Pauwels, 1980). While it has been hypothesised that bacterial infections may play a role in the induction and exacerbation of asthma, it has been considered that exacerbation of asthma is predominantly triggered by viral infection. Indeed, the clinical effect of bacterial vaccines in the treatment of asthma has been questioned leading to international (WHO) recommendations that bacterial vaccines have no role in modern asthma treatment.

Despite massive amounts of research focused on therapeutic asthma intervention and treatment, the condition remains a major, costly and growing problem in modern Westernised societies.

SUMMARY

Broadly stated, the present application stems from the recognition by the applicants that Non-typeable *Haemophilus influenzae* (NTHi) can act as a trigger for severe asthma as a result of persistent colonisation and/or recurrent exposure to NTHi. In particular, applicants have found that IgE antibody to NTHi is a highly significant mediator of asthma (often in a complex multi-factorial situation). Without being limited by theory, it is believed by the applicants that the reduction of inhaled/colonising NTHi in the lower airways reduces or essentially avoids the activation of mechanisms that trigger asthma. By reducing the induction of asthma, therapy with NTHi vaccine as described herein may also reduce asthma treatment needs and associated asthma medication.

Hence, in an aspect of the present application there is provided a method for prophylaxis or treatment of asthma in an individual, comprising administering to the individual an effective amount of an NTHi vaccine.

The vaccine can be any NTHi vaccine which induces an effective immune response against the bacteria. Typically, the vaccine will be an oral vaccine against NTHi and more usually, an oral killed NTHi vaccine.

In another aspect of the present application there is provided an oral vaccine for prophylaxis or treatment of asthma, the vaccine comprising at least one antigen of NTHi together with a physiologically acceptable carrier.

In another aspect of the present application there is provided the use of at least one antigen for generating an immune response against NTHi for prophylaxis or treatment of asthma in an individual.

The antigen can, for instance, be an antigen selected from the group consisting of killed or inactivated NTHi isolates, NTHi fractions and antigenic outer membrane components (eg., surface antigens or fragments thereof) of NTHi.

Typically, whole killed NTHi will be used in a vaccine or method for prophylaxis or treatment of asthma as described herein.

The individual can have diagnosed asthma or be an individual whom is deemed at risk of asthma such as a current or ex-smoker, an individual with recurrent airway infections, chronic cough and sputum (eg., as in chronic bronchitis), and/or intrinsic asthma. In at least one form, the individual will have one or more parameters indicative of exposure to NTHi such as an elevated neutrophil level, the presence of NTHi in sputum or saliva, and/or antibodies specific for NTHi. At least some embodiments of the present application have particular application in the prophylaxis or treatment of neutrophilic asthma.

Advantageously, administration of an NTHi vaccine in accordance with one or more embodiments of the present application can lead to a reduction in IgE antibodies and/or a reduction in the symptoms or severity of the asthma (eg., intrinsic or neutrophilic asthma) in the individual.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like that has been included in this specification is solely for the purpose of providing a context for the present application. It is not to be taken as an admission that any or all of these matters form part of the prior art base or were common general knowledge in the field relevant to the present application as it existed anywhere before the priority date of this application.

The features and advantages of the present application will become further apparent from the following detailed description of embodiments thereof.

BRIEF DESCRIPTION OF THE ACCOMPANYING DRAWINGS

DETAILED DESCRIPTION

Figure 1:
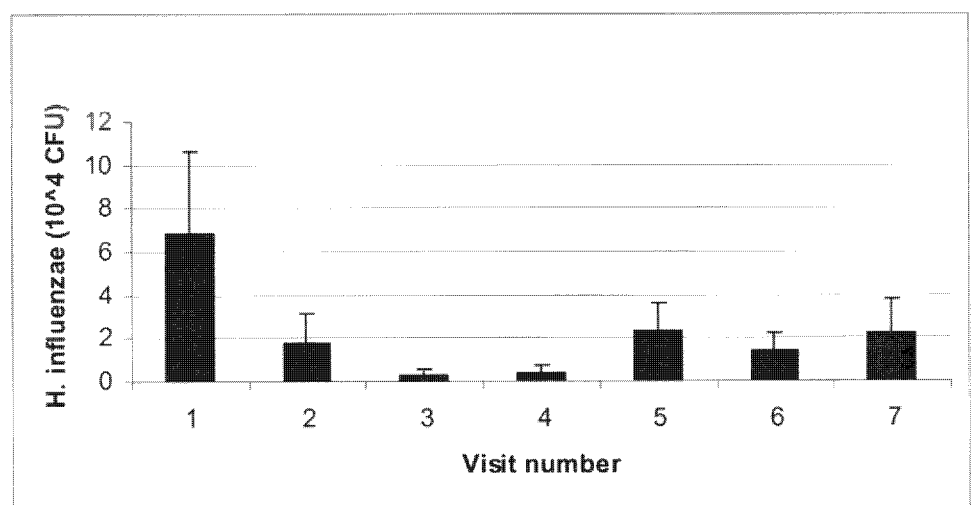
FIG. 1 is a graph showing mean number of NTHi isolated in gargle of a placebo study group.

Asthma is defined clinically by wheeze, reversible airways obstruction and bronchial hyperactivity. The commonest cause of asthma is IgE mediated hypersensitivity to inhaled allergens resulting in the classification of asthma as "extrinsic" or "intrinsic". However, individuals with long-standing asthma can develop cough and sputum stemming from lung damage and associated recurring infection of the airways. There are also, for example, bronchitic individuals with longstanding cough and sputum who develop wheeze, and individuals with recurrent asthma and airways infection.

Conventionally in asthma studies care has been taken to study discrete groups and generally, subjects with clearly defined asthma (eg., classical extrinsic asthma) are separated from other groups (eg., those with smoking-related airways disease) leading to the studies being conducted on defined groups of asthmatics in isolation of other groups of asthmatics. However, this is an artificial categorization and rather, it is more realistic to view asthma as a spectrum of airways disease as illustrated in Scheme 1.

Scheme 1: Spectrum of asthma disease

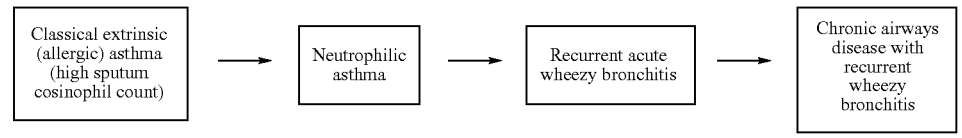

Various Different observations have been made with respect to these different clinical manifestations of asthma. In brief, these can be summarised as follows.

The induction of IgE antibody to inhaled antigens (eg., pollens) gives rise to classical allergic asthma in which allergen-specific IgE binds to mast cells causing degranulation of the mast cells and releasing of mediators such as histamine that give rise to allergic symptoms.

Colonisation of damaged airways and intermittent viral infection can lead to neutrophil flux into the bronchus (acute bronchitis) (usually associated with wheeze—thought to follow "inflammation" of the bronchus).

Smoking leading to lung damage can render the subject prone to infection of the airways.

However, many asthma subjects with clinically diagnosed asthma are 'mixed' with respect to these components and it is proposed that this spectrum of asthma disease can be reconciled by recognition that different pathogenic pathways can lead to asthma and that these pathways can co-exist. In particular, without being limited to theory, it is thought by the applicants that the dominant cause of wheeze in many asthmatics without demonstrable classical allergen hypersensitivity (eg., negative tests for IgE antibody to house dust, pollens and the like, and/or whom have elevated eosinophil counts) is due to an IgE antibody mediated reaction to colonising and/or recurrent exposure NTHi in conjunction with the ability of NTHi to induce and activate neutrophils. Specifically, NTHi vaccine can reduce the load of NTHi to the small airways, and provide effective treatment for so-called "intrinsic asthma".

More broadly, benefit from NTHi vaccine can be derived by those individuals exhibiting one or more parameters indicative of exposure to NTHi such as elevated neutrophil levels (with or without elevated eosinophil levels), current NTHi infection as for instance indicated by NTHi in sputum or saliva and/or NTHi specific antibody, and those individuals with damaged airways such as arising from smoking (chronic pulmonary obstructive disease (COPD)) or chronic bronchitis (particularly those individuals with wheeze). It is recognised, for instance, that individuals with damaged airways are highly prone to infection/colonisation by NTHi and other bacterial pathogens. While damage to airways classically follows smoking, extrinsic asthma can also damage the airways (hence, later onset of cough and sputum associated with NTHi infection). Benefit may also occur in asthmatic individuals with combined mechanisms (eg., atopic subjects with IgE antibody to NTHi), and the treatment of asthma and asthma symptoms in general as a result of decrease or avoidance of induction of IgE production resulting from exposure to NTHi.

Antibody levels can be measured in blood, serum, plasma, sputum or saliva samples using any suitable conventionally known assay protocol including enzyme linked immunosorbent assay (ELISA) or other immunoassay. NTHi-specific antibody can be selected from one or more of IgA, IgM, IgG and IgE and subclasses thereof, such as IgG1 and/or IgG3. Total IgE and/or NTHi specific IgE antibody will generally be measured in sputum or saliva sample. Neutrophil levels can also be measured in saliva or sputum using any appropriate conventionally known assay including microscopic evaluation following cell staining. Similarly, any suitable method known in the art can be employed to determine NTHi counts/level of NTHi infection. Antibody levels, neutrophil levels and NTHi counts can be compared against corresponding reference level(s) derived from classical extrinsic asthmatics (eg., exhibiting eosinophilic and/or hyper-responsiveness) or for example, a non-asthmatic control or other suitable reference group. Statistical methods for differentiating asthma groups are for instance, described in Simpson et al, 2006.

The vaccine utilised in a method of the present application will typically contain whole killed or inactivated (e.g., attenuated) NTHi isolate(s) (e.g., formalin-killed). However, soluble or particulate NTHi antigen comprising or consisting of outer cell membrane and/or surface antigens can be utilised as well, or instead of, whole killed organisms. In one or more embodiments, the outer cellular membrane fraction or membrane protein(s) of the selected NTHi isolate(s) will be utilised. For instance, NTHi OMP P6 is a highly conserved 16-kDa lipoprotein (Nelson et al., Cloning and sequencing of *Haemophilus* influenza outer membrane protein P6. *Infect. Immun.* 1988; 56: 128-134) which is a target of human bactericidal antibody and induces protection both in humans and in animal models. In chronic pulmonary obstructive disease (CPOD), OMP P6 has been shown to evoke a lymphocyte proliferative response that is associated with relative protection from NTHi infection (Abe et al., Lymphocyte proliferative response to P6 of *Haemophilus influenzae* is associated with relative protection from exacerbations of chronic obstructive pulmonary disease. *Am J Respir Crit Care Med* 2002; 165: 967-71). Accordingly, OMP P6 or any other suitable outer membrane NTHi proteins, polypeptides (eg., P2, P4 and P26) or antigenic fragments of such proteins or polypeptides can find application in the NTHi vaccine.

Soluble and/or particulate antigen can be prepared by disrupting killed or viable selected NTHi isolate(s). A fraction for use in the vaccine can then be prepared by centrifugation, filtration and/or other appropriate techniques known in the art. Any method which achieves the required level of cellular disruption can be employed including sonication or dissolution utilising appropriate surfactants and agitation, and combination of such techniques. When sonication is employed, the isolate can be subjected to a number of sonication steps in order to obtain the required degree of cellular disruption or generation of soluble and/or particulate matter of a specific size or size range.

The non-typeable *H. influenzae* isolate HI-164 (Hunter Immunology Limited, Frenchs Forest, N S W 2086, Australia) is particularly suitable for use in vaccines for the prophylaxis or treatment of asthma as described herein. NTHi-164 was deposited with the National Measurement Institute (NMI) in Melbourne, Australia on Aug. 13, 2008 and assigned deposit no. V08/021002.

The vaccine will typically comprise the selected bacterial isolate(s) and/or antigens in an amount of from about 0.1% to 100% w/w of the vaccine composition. An effective dosage of the vaccine will take into account the proposed mode of delivery and nature of the vaccine (eg. powder, liquid, aerosol delivery etc). For whole killed vaccines, the dosage of the, or each, bacterial isolate administered will typically be in a range of about $10^9$ to about $10^{12}$ killed bacteria, and more preferably from about $10^{10}$ to about $10^{11}$ killed bacteria. The optimum dosage of the vaccine can be determined by administering different dosages to different groups of test mammals, prior to subsequently infecting the animals in each group with NTHi, and determining the dosage level required to achieve satisfactory clearance of the pathogen.

The vaccine can be administered in accordance with any regimen suitable for generating an effective immune response against NTHi infection. For example, a single dose of the vaccine can be administered once per year pre-winter. One or more "booster" doses of the vaccine administered at an interval of a number of weeks or months may also be given. Alternatively, a number of doses of the vaccine maybe administered over the course of a number of weeks in order to generate an effective immune response against infection and/or colonisation by NTHi.

The vaccine itself can be a freeze-dried or lyophilised vaccine reconstituted utilising a physiologically acceptable buffer or fluid. The vaccine can also contain one or more anti-caking agents, preservatives such as thimerosal or which are otherwise suitable for the proposed mode of administration, stabilisers such as amino acids and sugar moieties, sweetening agents such sucrose, lactose or saccharin, surfactants, pH buffering agents and pH modifiers such sodium hydroxide, hydrochloric acid, monosodium phosphate and/or disodium phosphate, a pharmaceutically acceptable carrier such as physiologically saline, solvents and dispersion media and isotonic preparations. The vaccine can also comprise one or more adjuvants. Suitable adjuvants include for instance cholera toxin B subunits and conventionally known alum adjuvants. Typically, although not exclusively, the vaccine is non-adjuvanted.

Use of such ingredients and media in vaccines is well known in the art. Except insofar as any conventional media or agent is incompatible with the NTHi isolate(s) or antigens, or the proposed mode of administration, their use the vaccines that can be employed in methods embodied by the present application is specifically encompassed. Supplementary active agents for boosting the immune response including for instance, probiotic microorganisms, fractions and biological products thereof, and appropriate cytokines, can also be included to the vaccine. Pharmaceutically acceptable carriers and combinations of ingredients useful in vaccine compositions of the present application may for instance be found in handbooks and texts well known to the skilled addressee such as "Remington" The Science and Practice of Pharmacy (Mack Publishing Co., 1995)", the contents of which is incorporated herein in its entirety by reference. Specific examples of adjuvants include cholera toxin B subunit and conventionally known alum adjuvants.

The oral killed bacterial vaccine can be administered as a dry powder or in liquid form. Administration can for example be achieved by injection (eg. subcutaneous, or intravenous), orally such as by dosage unit form (eg tablet, capsule or dosed liquid form) instillation, or as a spray.

Particularly suitable forms of NTHi vaccine that can be administered in accordance with one or more embodiments of the present application include enterically coated tablets, capsules and dragees.

The individual to whom the vaccine is administered in accordance with the present application will normally be a human being although the vaccine may also be administered to any suitable mammalian asthma model. The present application is further described below by way of non-limiting Examples.

EXAMPLE 1

Subjects with Chronic Airways Disease have High Levels of IgE Antibody to NTHi

A study was performed in which subjects with chronic obstructive pulmonary disease (COPD) and an age-matched control group were assessed for levels of total IgE and NTHi-specific IgE in saliva, serum and sputum. A physical examination and a comprehensive questionnaire which included data on sex, age, smoking habits, and respiratory symptoms were completed. Use of corticosteroids and antibiotics were recorded from all subjects. Lung function was assessed by spirometry. None of the healthy controls were active smokers or had a history of ever having smoked. All but one of the subjects in the COPD group exhibited wheeze. Wheeze was defined as a wheezing or whistling sound in the chest at any time. None of the subjects studied had a respiratory infection within the preceding month. All patients were clinically stable. Saliva and bloods samples were collected.

1.1 Methodology
1.1.1 Saliva

Whole paraffin stimulated saliva was collected for 10 mins in ice-chilled tubes by mild suction, clarified by centrifugation at 20,000×g for 20 mins at 4° C. and the clear supernatant was kept frozen at −70° C. until analysed.

1.1.2 Serum

Ten milliliters of blood was collected by routine venipuncture and allowed to clot at room temperature, centrifuged at 5,000×g at 4° C. for 10 mins, and serum stored at −70° C. until analysed.

1.1.3 Sputum Sol.

In general, subjects were instructed to expectorate on arising and to keep samples refrigerated. Sputum samples were assessed for oropharyngeal contamination by microscopic examination according to the criteria described by Courcol et al (1985). Sputum sol was prepared from acceptable samples by centrifugation at 4° C. for 60 mins at 30,000×g and stored at −70° C. until analysed.

1.1.4 Preparation of NTHi Antigens

A zwittergent extract of NTHi OMP was prepared as described by Murphy et al (1988). P6, a highly conserved 16-kDa lipoprotein of NTHi, was purified using preparative polyacrylamide gel electrophoresis (PAGE) by the sodium dodecyl sulphate (SDS) method as described by Kyd et al (1994). Peparative SDS-PAGE for purification of P6 was performed using a Bio-Rad 491 Cell (BioRad, Hercules, Calif.). SDS-PAGE was carried out using the PHAST System (Pharmacia Piscataway, N.J.) to analyse the OMP zwittergent and P6 fractions with 10-15% gradient gels. Low molecular weight standards (Pharmacia) were run on each gel. Gels were stained with coomassie blue and silver nitrate.

1.1.5 IgE Enzyme Linked Immunosorbant Assay (ELISA)

Goat anti-human IgE (Tago, Inc. CA) at a concentration of 2.0 µg/ml was used for the measurement of total IgE in samples. IgE antibodies were measured by ELISA. Briefly, flat-bottomed 96-well ELISA plates (Immunoplate I; Polysorp, Nunc, Roskilde, Denmark) were coated overnight at 4°

C. with 100 µl of antigen at the appropriate concentration in sodium-bicarbonate buffer (pH 9.6) or sodium-bicarbonate buffer alone. The wells were washed three times with PBS pH 7.2 containing 0.05% (v/v) Tween 20 (PBS/Tween) and then 100 µl of 1% (w/v) BSA (Radioimmunoassay grade; Sigma, St Lois, Mo.) in PBS/T was added and left for 60 min at 37° C. The wells were washed with PBS/T and then 100 µl of sample diluted in 1% BSA/PBS/T were added to each well. The plates were incubated for an additional 60 min at 37° C., after which they were washed and 100 µl of biotinylated goat anti-human IgE (Tago, Inc. California, USA) diluted 1:1000 in 1% BSA/PBS/T was added and incubated for another 60 min at 37° C. After washing, 100 µl of peroxidase-conjugated streptavidin (Tago) diluted 1:40,000 in 1% BSA/PBS/T was added to each well and incubated for 45 min at 37° C. After washing, 100 µl of enzyme substrate 3,3',5,5'-tetramethyl-benzidine (Sigma) in substrate buffer was added to each well and incubated for 15-30 min at room temperature. The reaction was stopped with 100 µl of sulphuric acid (1.0 M) and absorbance was read at 490 nm on an ELISA plate reader. Standard curves were generated by running five two fold dilutions of goat anti-human IgE (2.0 µg/ml) (Bioclone, Australia) for the measurement of total IgE in samples and pooled serum from 10 chronic bronchitic subjects for the measurement of OMP IgE and P6 IgE in samples. Standard curves and samples were tested in duplicate. The absorbance of samples in carbonate buffer wells was subtracted from each antibody coated well to give the final result. The sensitivity range for total IgE was 0.15-2.43 ng/ml. Checkerboard titrations were conducted to optimize all antibody concentrations and useful ranges for protein standard concentrations and sample dilutions.

1.2 Serum and Sputum IgE Levels in Control and Treatment Groups

Total IgE and NTHi IgE antibodies were measured by ELISA assay as described in Example 1.1.5. The patient profile is shown in Table 1a. The values obtained are shown in Table 1b (values presented represent the mean+/−SEM).

TABLE 1a

Subject profile

|  | Controls (9) | Chronic obstructive airways disease with asthma (11) |
|---|---|---|
| Age (yrs) | 33 (23-42) | 46 (23-61) |
| Smokers (%) |  |  |
| Current | 0 | 64 |
| Ex-smokers | 0 | 10 |
| FEV1 (L) | — | 2.6 (1.2-4.7) |

TABLE 1b

Total IgE, IgE to NTHi OMP, and IgE to NTHi P6 in subjects with recurrent airways infection and asthma

|  | Controls | | Chronic obstructive airways disease with asthma | | |
|---|---|---|---|---|---|
|  | Saliva | Serum | Saliva | Serum | Sputum |
| Total IgE (ng/ml) |  |  |  |  |  |
| Mean ± SE | 5.4 ± 0.7 | 401 ± 92 | 5.0 ± 0.4 | 438 ± 100 | 11.5 ± 1.6 |
| Median | 5.4 | 290 | 4.8 | 297 | 11.4 |
| Range | 1.6-9.3 | 210-1,093 | 2.4-7.0 | 131-1,172 | 4.1-21.3 |
| OMP IgE (EU/ml) |  |  |  |  |  |
| Mean ± SE | ND. | 14 ± 4 | 0.26 ± 0.05 | 79 ± 14 | 0.34 ± 0.9 |
| Median |  | 12 | 0.19 | 80 | 0.25 |
| Range |  | 2-35 | 0.11-0.66 | 11-176 | 0.11-1.16 |
| P6 IgE (EU/ml) |  |  |  |  |  |
| Mean ± SE | ND. | 10 ± 5 | ND. | 61 ± 15 | 0.33 ± 0.6 |
| Median |  | 7 |  | 36 | 0.25 |
| Range |  | 2-30 |  | 13-158 | 0.21-0.67 |

ND = Not detectable
EU = Elisa Units 1.3 IgE Levels and Allergic Airways Disease The relationship between IgE level and allergic respiratory disease in subjects was evaluated. The patient profile is shown in Table 2a. In brief, subjects with recurrent acute bronchitis with bronchospasm (most of whom smoke and have early chronic airways disease) were found to have high levels of IgE antibody irrespective of existence of allergic disease. Total IgE and NTHi specific IgE levels are shown in Table 2b (values presented represent the mean+/−SEM).

TABLE 2a

Subject profile

|  | Controls (9) | Chronic obstructive airways disease with asthma (17) |
|---|---|---|
| Smokers (%) (or ex-smokers) | 0% | 100% |
| FEV1 (L) | 1.95 (1.35-2.55) | 0.5 (0.2-1.14) |

TABLE 2b

Total IgE and IgE specific to NTHi antigens (OMP & P6)

| | Controls | | COPD | | |
|---|---|---|---|---|---|
| | Saliva | Serum | Saliva | Serum | Sputum |
| Total IgE (ng/ml) | | | | | |
| Mean ± SE | 4.0 ± 1.0 | 490 ± 118 | 8.5 ± 1.2 | 992 ± 224 | 11.8 ± 1.7 |
| Median | 2.8 | 401 | 8.4 | 784 | 9.6 |
| Range | 1.1-9.4 | 119-1,199 | 2.2-20.6 | 112-3,822 | 1.9-22.7 |
| OMP IgE (EU/ml) | | | | | |
| Mean ± SE | 0.15 ± 0.03 | 15 ± 3 | 0.26 ± 0.04 | 257 ± 54 | 0.17 ± 0.04 |
| Median | 0.13 | 15 | 0.16 | 202 | 0.15 |
| Range | 0.08-0.27 | 5-32 | 0.11-0.56 | 33-801 | 0.09-0.40 |
| P6 IgE (EU/ml) | | | | | |
| Mean ± SE | ND. | 86 ± 36 | ND. | 182 ± 43 | ND. |
| Median | | 55 | | 122 | |
| Range | | 6-361 | | 3-523 | |

ND = Not detectable
EU = Elisa Units 1.4 Discussion

The results presented in Examples 1.2 and 1.3 show no significant difference in the level of total IgE in control and COPD groups in serum and saliva. However, a significant increase in IgE OMP antibody in the COPD group compared to control group (P<0.01) was found, and both IgE OMP antibody and IgE P6 antibody were detected in sputum. The results show that NTHi-specific IgE antibody is common in serum and secretions in individuals with chronic airways disease and asthma (wheeze).

Subjects that had mild to severe COPD and were treated with the oral vaccine in the active treatment group were found to have a 50% reduction in the usage of bronchodilator therapies. Moreover, eosinophil counts following the administration of a triple course of oral NTHi vaccine therapy were found to be significantly reduced in the active treatment group only. In conclusion, the oral NTHi therapy reduces the usage bronchodilator therapies in acute episodes and also reduces eosinophil counts which are associated with allergic reactions specific to NTHi.

EXAMPLE 2

A placebo-controlled double-blind clinical study was performed in which 64 subjects on the basis of having smoked at least 10 cigarettes per day for the past two years were recruited and allocated to oral NTHi therapy or placebo treatment groups in a double-blind study. Subjects were randomised into placebo and active groups and were given three courses of study medication at monthly intervals. Each course consisted of two tablets per day for three days. The active tablets each contained 45 mg of formalin-killed NTHi (equivalent to $10^{11}$ killed bacteria per active tablet). Blood, saliva, gargles, throat swabs, and nasal swabs (for microbiological assessment) were collected at seven fortnightly visits.

2.1 Detection of NTHi and Measurement of NTHi-Specific IgG

Surprisingly, measurements in the placebo-treated and vaccine-treated groups over the winter period detected NTHi in both groups indicating random exposure to the bacterium. FIG. 1 shows the mean level of NTHi in the gargles of the placebo group at each visit.

NTHi-specific IgG was measured in serum and saliva by ELISA assay. Briefly, wells of 96-well Nunc Maxisorp plates were coated with *H. influenzae* 164 sonicate antigen preparation. After incubation overnight at 2-8° C. the plates were washed and samples of serum or saliva at various dilutions were added. Following incubation at room temperature for 60 minutes, the plates were washed and horseradish peroxidise-conjugated anti-human IgG antibody (Chemicon catalogue number AP112P) was added. After incubation for a further 60 minutes at room temperature the plates were washed and TMB substrate (Biomediq catalogue number 50-76-00) was added prior to an additional incubation for 10 minutes at room temperature and the reaction being stopped by addition of 1M phosphoric acid. Absorbance was read on a BioRad microplate reader on dual wavelength mode with a primary filter of 450 nm and reference filter of 655 nm. A standard curve was used to determine the ELISA units in each sample.

Figure 2:
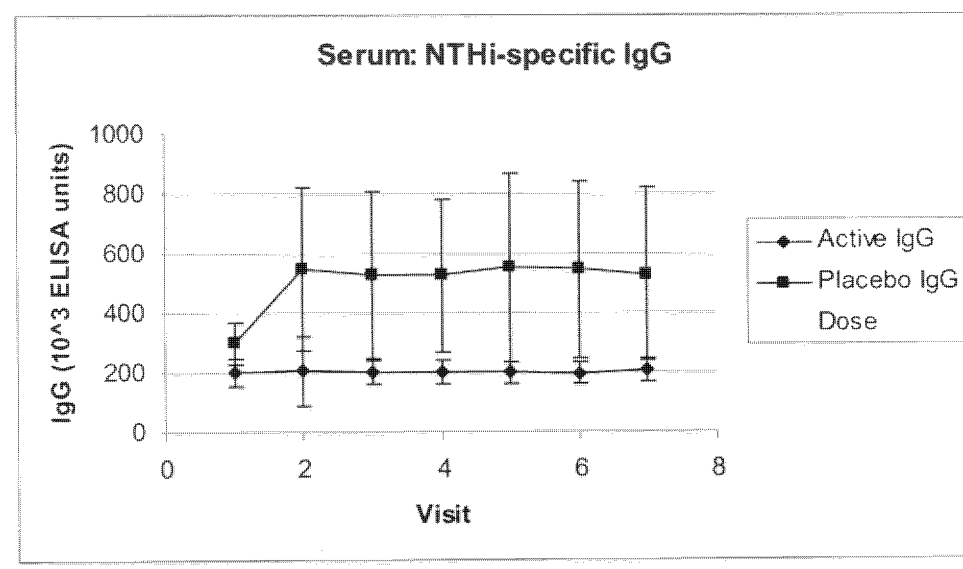
FIG. 2 is a graph showing serum NTHi-specific IgG levels in the placebo group and a treatment group immunized with an oral killed NTHi vaccine.
Figure 3:
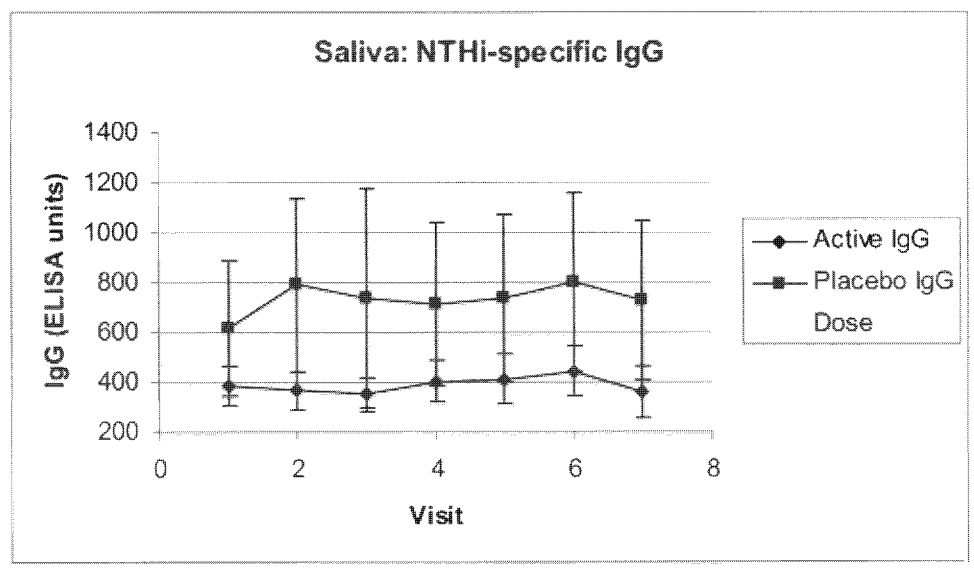
FIG. 3 is a graph showing saliva NTHi-specific IgG levels in the placebo group and the treatment group immunized with an oral killed NTHi vaccine.

Levels of NTHi-specific IgG in serum and saliva in the placebo group were higher and more variable than the levels in the vaccine-treated group (see FIG. 2 and FIG. 3). Applicants believe this because NTHi reaching the lower airways in the placebo group results in systemic production of IgG and that NTHi was essentially prevented from reaching the lower airways in the vaccine treated group. To test this, plots were prepared of relationship between the number of visits at which NTHi was detected in the gargle and the Log change in serum IgG between visits 1 and 6. Placebo and active subjects were grouped according to whether they had 0-1 visits or 2-4 visits where NTHi was found in the gargle. In the placebo group, positive increases in serum IgG were associated with increased number of NTHi detections. This was not found in the active treatment group. The difference between the placebo and active change in IgG was statistically significant (p=0.0186) indicating the serum IgG in the placebo group was indeed generated by NTHi as a result of the bacteria reaching the lower airways. Moreover, the more NTHi present in the placebo washings, the higher the IgG antibody level. This is also believed to apply to the appearance of salivary NTHi-specific IgG in the placebo group.

2.2 Discussion

Serum IgG antibody as a marker for the efficacy of the vaccine was measured. An apparent lack of an IgG response in the vaccine-treated group was found while the placebo treated group of patients showed an increase in serum IgG. Without being limited by theory, it is believed by the applicants that the increase in IgG observed in the placebo group is reflecting an immune response to infecting bacteria reaching the lower airways where uptake of the bacteria by antigen-presenting cells and transport to draining lymph nodes induces an anti-bacterial IgG response. In contrast, the lack of such a response in the vaccine-treated group indicates that the bacteria are being essentially prevented (by a mucosal vaccine-specific immune response) from reaching the lower airways. A comparison of the IgG response in subjects with NTHi detected in the upper airways at 0-1 or 2-4 visits also showed the increase in IgG in the placebo group but not in the active (vaccine) treatment group. This suggests that serum IgG measurement following oral vaccination with NTHi reflects exposure to infection and the degree to which this is prevented by mucosal immunization. The saliva IgG response reflected that seen in the serum.

Overall, this study demonstrates detection of NTHi in the upper respiratory tract of subjects in both the treatment and placebo groups, and that treatment with oral killed NTHi vaccine therapy led to a reduction of NTHi-specific IgG in serum and saliva in the treatment group indicating the vaccine was successful in limiting or preventing access of NTHi to the lower airways (ie., less allergen to initiate asthma).

Thus, only in the placebo group did NTHi access the lower airways as evidenced by stimulation of IgG antibody, and oral 'immunisation' with NTHi vaccine reduced NTHi allergen in the airways

EXAMPLE 3

Killed NTHi Vaccine Orally Administered to Subjects with Mild, Moderate or Severe Airway Disease Reduce Usages of Anti-Asthma Therapy One hundred and forty human subjects with mild-to-moderate or moderate-to-severe airway disease were recruited into a double blind, placebo-controlled study to assess the effect of an oral killed non-typeable *Haemophilus influenzae* (NTHi) vaccine on number and severity of wheezy reversible airways obstruction, and usage of concomitant medication as well as the presence of NTHi and other bacteria in the airways.

A reduction in use of anti-asthma-type medication (bronchodilators, steroids etc) and reduced infection by NTHi was found in the treatment group compared to the control group. In particular, a specific reduction of NTHi within the airways of subjects with high IgE antibody levels (serum and secretions) to NTHi, and a reduction in asthma symptoms with a consequential reduction in the need for asthma medication were obtained.

Although the present application has been described with reference to particular examples, it will be appreciated by those skilled in the art that numerous variations and/or modifications may be made without departing from the spirit or scope of the present application. The present embodiments are, therefore, to be considered in all respects as illustrative and not restrictive.

The invention claimed is:

1. A method for treatment of acute exacerbations of asthma in an individual with chronic airways disease characterised by reversible airways obstruction, the method comprising orally administering an effective amount of a vaccine preparation to the individual, wherein the vaccine preparation comprises an oral whole cell killed non-typeable *Haemophilus influenzae* (NTHi) vaccine, and wherein the asthma is characterized by an elevated eosinophil level and an elevated neutrophil level in sputum or saliva.

2. The method according to claim 1 wherein said asthma is intrinsic asthma.

3. The method according to claim 1 wherein said asthma is neutrophilic asthma.

4. The method according to claim 1 wherein said individual exhibits one or more parameters indicative of exposure to NTHi selected from the group consisting of the presence of NTHi in sputum or saliva, and the presence of antibodies specific for NTHi.

5. The method according to claim 4 wherein said individual exhibits NTHi specific antibodies.

6. The method according to claim 5 wherein said antibodies are IgE antibodies.

7. The method according to claim 1 wherein said oral killed vaccine comprises one or more whole killed NTHi isolates.

* * * * *